United States Patent [19]

Qin et al.

[11] Patent Number: 5,670,655

[45] Date of Patent: Sep. 23, 1997

[54] METHOD FOR ANALYZING ISOMERS OF ENALAPRIL AND ENALAPRILAT

[75] Inventors: Xue-Zhi Qin, Lansdale, Pa.; Giuseppina Visentini, Quebec, Canada; Qingxi Wang, Lansdale, Pa.

[73] Assignee: Merck & Co. Inc., Rahway, N.J.

[21] Appl. No.: 711,575

[22] Filed: Sep. 10, 1996

Related U.S. Application Data

[60] Provisional application No. 60/003,825 Sep. 15, 1995.
[51] Int. Cl.[6] ................................................ C07D 207/04
[52] U.S. Cl. ................................................ 548/533
[58] Field of Search ................................................ 548/533

[56] References Cited

U.S. PATENT DOCUMENTS

4,374,829  2/1983  Harris et al. ........................... 424/177

OTHER PUBLICATIONS

Thomas, B.R., et al., "Evaluation of a Mixed Micellar Electrokinetic Capillary Electrophoresis Method for Validated Pharmaceutical Quality Control", J. of Liq. Chrom., vol. 16(9 & 10), pp. 1983–2006, 1993.

Smith, E.M., et la., "Angiotensin Converting Enzyme Inhibitors: Spirapril and Related Compounds", J. Med. Chem., vol. 32, pp. 1600–1606, 1989.

Qin et al., Journal of Chromatography, vol. 626, pp. 251–258 1992.

Qin et al., Journal of Chromatography A, vol. 707, pp. 245–254 1995.

Chemical Abstracts, 119:210883 1993.
Chemical Abstracts, 119:146730 1993.

*Primary Examiner*—Joseph McKane
*Assistant Examiner*—Richard S. Myers, Jr.
*Attorney, Agent, or Firm*—Valerie J. Camara; Mark R. Daniel

[57] ABSTRACT

The invention relates to a method for analyzing degenerates of enalapril maleate and enalaprilat, potent angiotensin converting enzyme inhibitors.

4 Claims, 9 Drawing Sheets

METHOD FOR ANALYZING ISOMERS OF ENALAPRIL AND ENALAPRILAT

This application claims priority of Provisional Application No. 60/003,825, filed Sep. 15, 1995.

BACKGROUND OF THE INVENTION

Enalapril is an angiotensin converting enzyme (ACE) inhibitor indicated for use in the treatment of hypertension. Enalapril is currently approved for marketing as enalapril maleate, as well in combination with hydrochlorothiazide. ACE inhibitors are also being studied in combination with calcium channel blockers.

Stability studies of dosage forms of enalapril have indicated the possibility of isomerization at the three chiral centers in enalapril. It is believed that these isomerization products could contribute to a mass balance problem with various enalapril-containing formulations. To provide information on the isomerization of SSS-enalapril, SSR- and SRS-enalapril isomers were synthesized using L-alanyl-D-proline and D-alanyl-L-proline dipeptides. These compounds can be used directly or indirectly as precursors to quantify any enalapril isomers formed. They could also be used to study the structure-activity relationship of enalapril.

SUMMARY OF THE INVENTION

This invention relates to a method for analyzing the degenerates of enalapril, specifically the SRS-enalaprilat and SSR-enalaprilat isomers. This invention also relates to SRS- and SSR-enalapril and SRS- and SSR-enalaprilat isomers useful in this method.

DETAILED DESCRIPTION OF THE INVENTION

Figure 1:
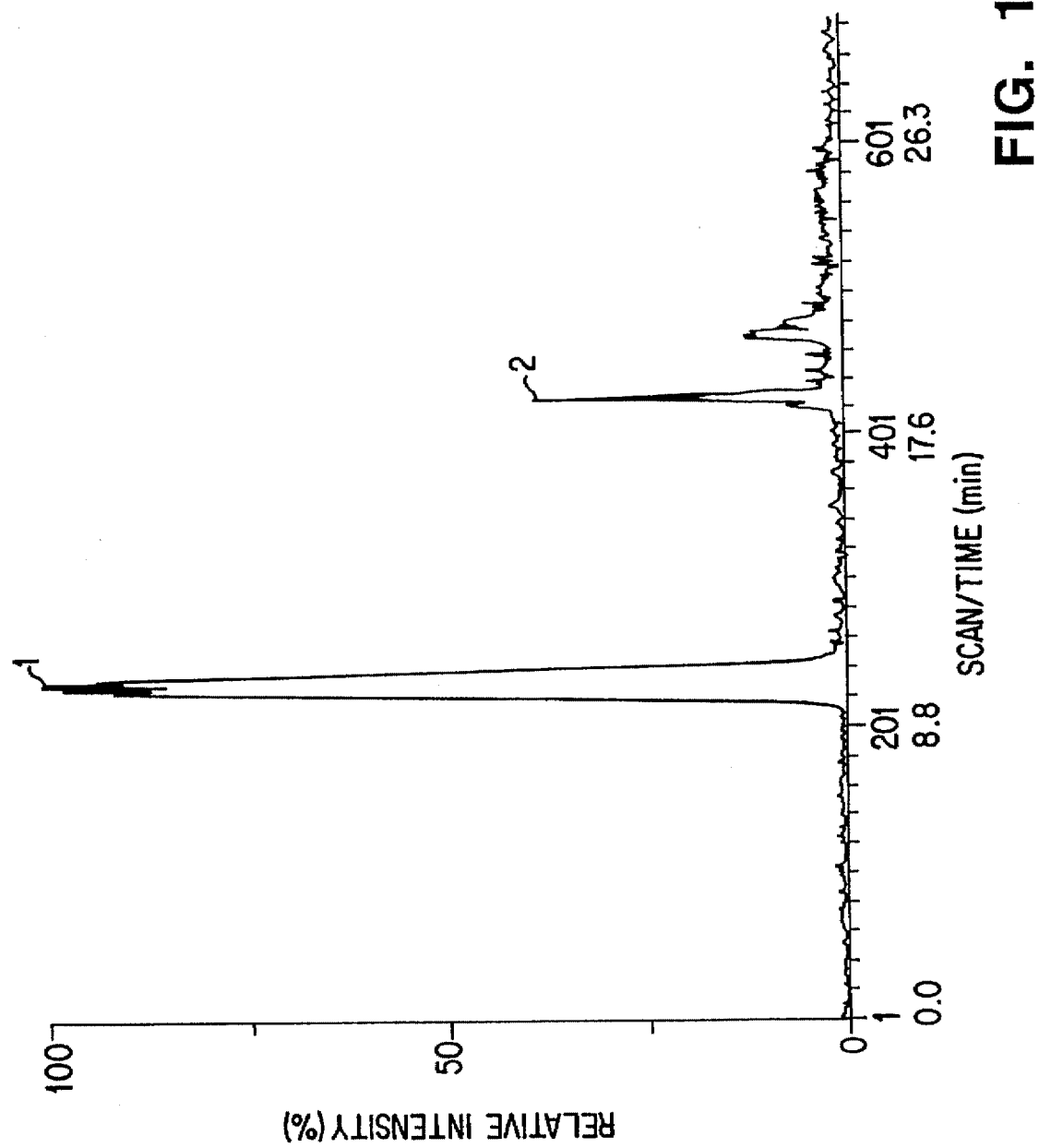
FIG. 1. Total ion current (TIC) profile of the product ion spectra of m/z 349 for the tablets of 5/180 enalapril-diltiazem stressed at 60° C. for four weeks.

This invention relates to a method for analyzing the degradates of enalapril comprising:

(a) stressing a composition containing enalapril;

(b) chromatographing the stressed composition of enalapril;

(c) comparing the chromatogram of stressed enalapril with all known enalapril degradates;

(d) analyzing the stressed composition by liquid chromatography-mass spectrometry to detect a molecular ion and fragmentation pattern for the unknown degradates;

(e) reacting a sample of enalaprilat with t-butyl lithium to form a mixture of diastereomers of enalaprilat;

(f) chromatographing the diastereomers of enalaprilat;

(g) comparing the chromatogram of stressed enalapril with the chromatogram for the mixture of diastereomers of enalaprilat;

(h) identifying the unknown enalapril degradate as a diastereomer of enalaprilat;

(i) synthesizing standards of enalaprilat SRS- and SSR-diastereomers;

(j) chromatographing the SRS- and SSR- diastereomers of enalaprilat; and (k) comparing the chromatograms of the SRS- and SSR-diastereomers of enalaprilat with the chromatogram of the stressed enalapril to identify which diastereomer of enalaprilat corresponds to the unknown degradate.

An embodiment of this invention is the method for analyzing the degradates of enalapril as recited above, wherein the composition containing enalapril is stressed by exposing the composition to a temperature range of about 40° C. to about 80° C. and a relative humidity of about 0% to about 75% for a period of about 2.5 weeks to about 6 months.

A second embodiment of this invention is the method for analyzing the degradates of enalapril as recited above, wherein the liquid chromatography is carried out using a C-8, 5µ 250×4.6 mm i.d. column using a gradient of acetonitrile and phosphate buffer.

A third embodiment of this invention is the method for analyzing the degradates of enalapril as recited above, wherein the sample of enalaprilat is treated with t-butyl lithium in tetrahydrofuran for a period of about 30 minutes, followed by hydrolysis to form a mixture of diastereomers of enalaprilat.

A compound which is SRS-enalapril or a pharmaceutically acceptable salt thereof.

A compound which is SSR-enalapril or a pharmaceutically acceptable salt thereof.

A compound which is SRS-enalaprilat or a pharmaceutically acceptable salt thereof.

A compound which is SSR-enalaprilat or a pharmaceutically acceptable salt thereof.

This invention relates to a method for analyzing two of the degenerates of enalapril, specifically the SRS- and SSR-enalapril and SRS- and SSR-enalaprilat diastereoisomers, to address the mass balance problem noted with enalapril that occurs over time. This invention also relates to SRS- and SSR-enalapril and SRS- and SSR-enalaprilat isomers useful in this method.

Enalapril-SSS maleate, enalapril DKP-SSS, enalaprilat-SSS, Enalaprilat-RSS and enalaprilat DKP-SSS were obtained from Merck Research Laboratories (Rahway, N.J.). L-analyl-D-proline TFA salt was provided by Medicinal Chemistry Department of Merck Research Laboratories (West Point, Pa.). Ethyl-2-oxo-4-phenylbutyrate, sodium cyanoborohydride, dry molecular sieves (5 Å) and Dowex 2×50 W strong acid ion exchange resin were obtained from Aldrich Chemical Company (Milwaukee, Wis.). Absolute ethanol, acetonitrile (Optima grade), dipotassium hydrogen phosphate (certified A.C.S. grade), potassium phosphate (certified A.C.S. grade), ammonia acetate (certified A.C.S. grade), triethylamine (certified A.C.S. grade), ethyl acetate (certified A.C.S. grade), pyridine, sodium chloride HPLC grade) and anhydrous sodium sulfate (HPLC grade) were obtained from Fisher Scientific (Philadelphia, Pa.). D-alanyl-L-proline was obtained from Sigma Chemical (St.

Luis, Mo.). All the chemicals were used as received. Deionized water with at least 18M-Ohm purified by Milli-Q system was used for the mobile phase, and the sample and standard preparation.

The development of HPLC methods was performed on a Hewlett-Packard (HP) 1090 system equipped with a Spectra Physics (SP) 100 variable wavelength UV detector. The LC/MS and LC/MS/MS studies were conducted on a PE/Sciex (Thornhill, Ontario) API III triple quadrupole mass spectrometer interfaced via a Sciex heated nebulizer probe to an HP1050 LC. The $^1$H and two dimensional COSY NMR spectra were obtained on Varian Unity 400 spectrometer. FAB mass spectra were obtained on a VG-7070 E mass spectrometer.

The HPLC conditions were: Spherisorb C8 column (5 μm particle size, 250×4.6 mm i.d.) purchased from Phase Sep. Inc.; column temperature (T) of 40° C.; mobile phase of 35% $CH_3CN$ and 65% 0.001M $KH_2PO_4$ (pH 2) (v:v); flow rate of 2 mL/min.; UV detection at 215 nm and injection volume of 50 μL.

Liquid chromatography conditions have been re-developed for the LC/MS study by the use of volatile buffer (e.g., ammonia acetate) in the mobile phase. Typical conditions are: column of Hamilton PRP-1 (250×4.1 mm i.d.); column T of 70° C.; flow rate of 0.7 to 1 mL/min.; gradient method containing solvent A of 5 to 10% $CH_3CN$ and 95 to 90% 20 mM $NH_4OAc$, and solvent B of $CH_3CN$ with the procedure:

0 to 5–10 min.: 100% A,
5–10 to 20 min.: 40% A, 60% B,
20 to 22 min.: 30% A, 70% B,
22 to 23 min.: 100% A;

and injection volume of 20 to 25 μL.

The LC/MS and LC/MS/MS were performed by the use of an Atmospheric Pressure Chemical Ionization (APCI) source in the positive ionization mode. [Buckley, J. A.; French, J. B., and Reid, N. M., *Can. Aeronaut. Space J.* 20, (1974), p. 231; Thomson, B. A., and Danylewch, M. L., *Proceedings of the 31st Annual Conference on Mass Spectrometry and Related Topics* (American Society for Mass Spectrometry, Boston, 1983), p. 852; Allen, M. H., and Shushan, B. I., *LC-GC* 10, (1992), p. 356 and references therein.] Introduction of samples were performed by applying LC conditions for LC/MS described above and for product ion LC/MS/MS analysis of ions of interest. The flow from the column passed through a diode array detector and then entered directly into the APCI probe for which the heater was maintained at 500° C. The corona discharge needle optimized at a current of 3 μA and the orifice voltage was set to 60 V. The nitrogen (99.99999%) nebulizer gas pressure and flow were kept at 60 psi and 0.6 L/min., respectively. The auxiliary gas pressure (nitrogen 99.99999%) was set to 1.0 L/min. The curtain gas flow (nitrogen 99.99999%) was set at 1.2 L/min. The collision gas used for LC/MS/MS analyses was argon (99.99999%) at a collision gas thickness of about $600×10^{12}$ atoms/cm$^3$ and the collision energy was 30 eV.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. The preferred salts of this invention include, but are not limited to: potassium, sodium, calcium and ammonium salts of the ACE inhibitor and/or AII receptor antagonist.

The following examples illustrate the method disclosed in the instant invention, and as such are not to be considered as limiting the invention set forth in the claims appended hereto.

EXAMPLE 1

Analysis of Degradates of Enalapril

Step A: Detection of an Extra Species in Stressed Enalapril-Diltiazem (5/180 mg) Tablets An extra species was detected in some stressed enalapril-diltiazem (5/180 mg) tablets. A chromatogram of this enalapril-diltiazem combination, stressed at 60° C. for four weeks, was obtained using the following HPLC conditions: Spherisorb C8 (5μ) 250×4.6 mm i.d. at 40° C. using 35:65 $CH_3CN$ to 0.001M $KH_2PO_4$ (at pH2) detecting at 215 nm. Enalapril eluted at 14.3 min. Enalaprilat (diacid, a hydrolysis degradate of enalapril) eluted at 3.5 min. The extra, unknown species eluted at about 4 min. This extra species was also observed in the enalapril/diltiazem tablets stressed at 30° C. for 18 months as shown in Table 1, in which the extra species is designated as an enalapril-related degradate.

TABLE 1

The Amount of the Enalapril-Related Degradate Observed in Tablets of Enalapril-Diltiazem Stressed at 30° C./Ambient Humidity for 18 months

| Ref # | Sample Package | % Relative to Diacid Standard |
|---|---|---|
| L011 | 210 mL, HDPE | 0.32 |
|  | 75 mL, HDPE | 0.12 |
|  | 30 mL, HDPE | not detected (<.1%) |
|  | Aluminum Blister | 0.44 |
| L012 | 210 mL, HDPE | 0.15 |
|  | 75 mL, HDPE | not detected (<.1%) |
|  | 30 mL, HDPE | not detected (<.1%) |
|  | Aluminum Blister | 0.26 |

Note:
The Enalapril-related degradate has been found to have a retention time of 3.5 to 4 minutes.

Step B: Investigation of the Extra Species— Suggestion of the Enalaprilat Isomer An investigation was made, which indicated that the extra, unknown species was enalapril—related and especially, enalaprilat—related. The investigation results are listed in Table 2 below. As shown, the extra, unknown specie was not observed in the initial and stressed 0/180 and 0/0 enalapril/diltiazem tablets, in which there was no enalapril. It was not observed in the initial 5/180 enalapril/diltiazem tablets, but observed in some of the stressed 5/180 enalapril/diltiazem tablets. The amount of this species varied depending on the stress conditions. This species was also observed after stressing enalapril maleate bulks and enalaprilat standard. All these facts indicate that it is enalapril-related, and especially, enalaprilat—related. Since it eluted near enalaprilat-SSS (diacid) in HPLC, it was reasonably thought that this extra species could be a diastereomer of enalaprilat. This assumption was supported when the chromatogram of the 5/180 enalapril-diltiazem tablets (stressed: 60° C. for four weeks) was compared with the chromatogram of enalaprilat—RSS standard using the same HPLC conditions as recited above in Step A, except the eluants were used in a 30:70 ratio $CH_3CN:KH_2PO_4$. The chromatogram of the RSS standard shows three peaks. The major peak at 4.31 min. is assigned to the RSS isomer, which eluted after the SSS isomer (4.14 min.) and before the extra, unknown species (5.26 min.). This excluded the extra, unknown species from the RSS isomer of enalaprilat. The other two peaks in the chromatogram of the RSS standard are: (1) the peak at 4.92 min., which is assigned to the RSS-enalaprilat diketopiperidine (RSS-DKP); and (2) the peak at 5.24 min. The peak at 5.24 min. is a polar species similar to that of the RSS compound. Since it is a polar species, it cannot be any diastereoisomer of enalaprilat-DKP, which should be non-polar. Thus, the peak at 5.24 min. was considered to be an enalaprilat isomer (confirmed by LC/MS study later). Since the extra, unknown species eluted at the retention time of 5.26 min., nearly the same as the enalaprilat-isomer eluting at 5.24 min. in the chromatogram, the extra species was thought to be an enalaprilat isomer.

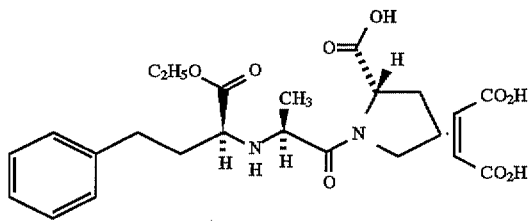

Enalapril maleate (SSS-isomer)

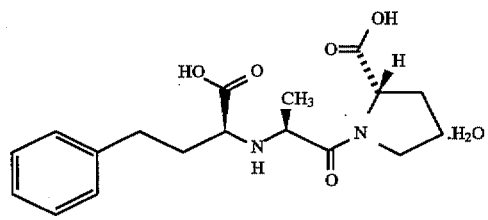

Enalaprilat (SSS-isomer)

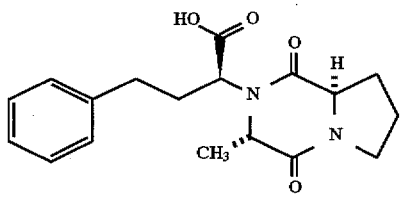

Enalaprilat-DKP (SSS-isomer)

TABLE 2

| samples enalapril/ diltiazem | stress conditions | unknown species | area % rel. to enalapril |
|---|---|---|---|
| 0/180 | initial | no | 0 |
| 0/180 | 80° C., glass vial, 8 weeks | no | 0 |
| 0/180 | 40° C., 75% rel. hum., open dish, 4 weeks | no | 0 |
| 0/0 | 80° C., glass vial, 8 weeks | no | 0 |
| bulk enalapril | 60° C., glass vial, 4 weeks | yes | <<0.1 |
| bulk enalapril | 40° C., 75% rel. hum., open dish, 4 weeks | yes | <<0.1 |
| bulk diltiazem | initial | no | 0 |
| 5/180 | initial | no | 0 |
| 5/180 | 40° C., 75% rel. hum., HDPE, 6 months | yes | 0.2 |
| 5/180 | 80° C., glass vial, 8 weeks | yes | 1.7 |
| enalaprilat | 80° C., open dish, 2.5 weeks | yes | 0.2* |
| enalapril/ felodipine | 60° C., open dish, 5 months | yes | 1.2 |

*relative to enalaprilat

Step C: Liquid Chromatography-Mass Spectrometry Analysis of the Extra Species found in Stressed Tablets of Enalapril Liquid Chromatography conditions have been developed for the LC/MS study using volatile buffer (ammonia acetate) in the mobile phase. Typical conditions are:

| | |
|---|---|
| Column: | Hamilton PRP-1, 4.6 mm × 25 cm |
| Column Temperature: | 70° C. |
| Flow rate: | 0.7 mL/min |
| (Alternative flow rate) | (1.0 mL/min) |
| Eluants: | |
| Solvent A: | 5% $CH_3CN$ and 95% 20 mM $NH_4OAc$ or |
| (Alternative eluant) | (10% $CH_3CN$ and 90% 20 mM $NH_4OAc$) |
| Solvent B: | $CH_3CN$ |
| Gradient: | 0 to 10 min, 100% A; |
| (Alternative gradient conditions) | 10 to 20 min, 40% A 60% B; 20 to 22 min, 30% A 70% B; 22 to 23 min, 100% A or (0 to 5 min, 100% A; 5 to 20 min, 40% A 60% B; 20 to 22 min, 30% A 70% B; 22 to 23 min, 100% A.) |
| Injection volume: | 20 μL or |
| (Alternative injection volume) | (25 μL) |

The LC/MS and LC/MS/MS studies were conducted on a PE/Sciex API III triple quadrupole mass spectrometer by the use of an Atmospheric Pressure Chemical Ionization (APCI) source in the positive ionization mode. Introduction of samples was performed by applying the HPLC method described above with full scan LC/MS analysis and product ion LC/MS/MS analysis of ions of interest. The flow rate was about 0.7 to about 1 mL/min. The flow from the column passed through a diode array detector and then entered directly into the APCI probe for which the heater was maintained at 500° C. The corona discharge needle optimized at a current of 3 μA and the orifice voltage was set to 60 V. The nitrogen (99.99999%) nebulizer gas pressure and flow were kept at 60 psi and 0.6 L/min, respectively. The auxiliary gas pressure (nitrogen 99.99999%) was set to 1.0 L/min. The curtain gas flow (nitrogen 99.99999%) was set at 1.2 L/min. The collision gas used for LC/MS/MS analyses was argon (99.99999%) at a collision gas thickness of about $600 \times 10^{12}$ atoms/cm$^3$ and the collision energy was 30 eV.

Figure 2A:
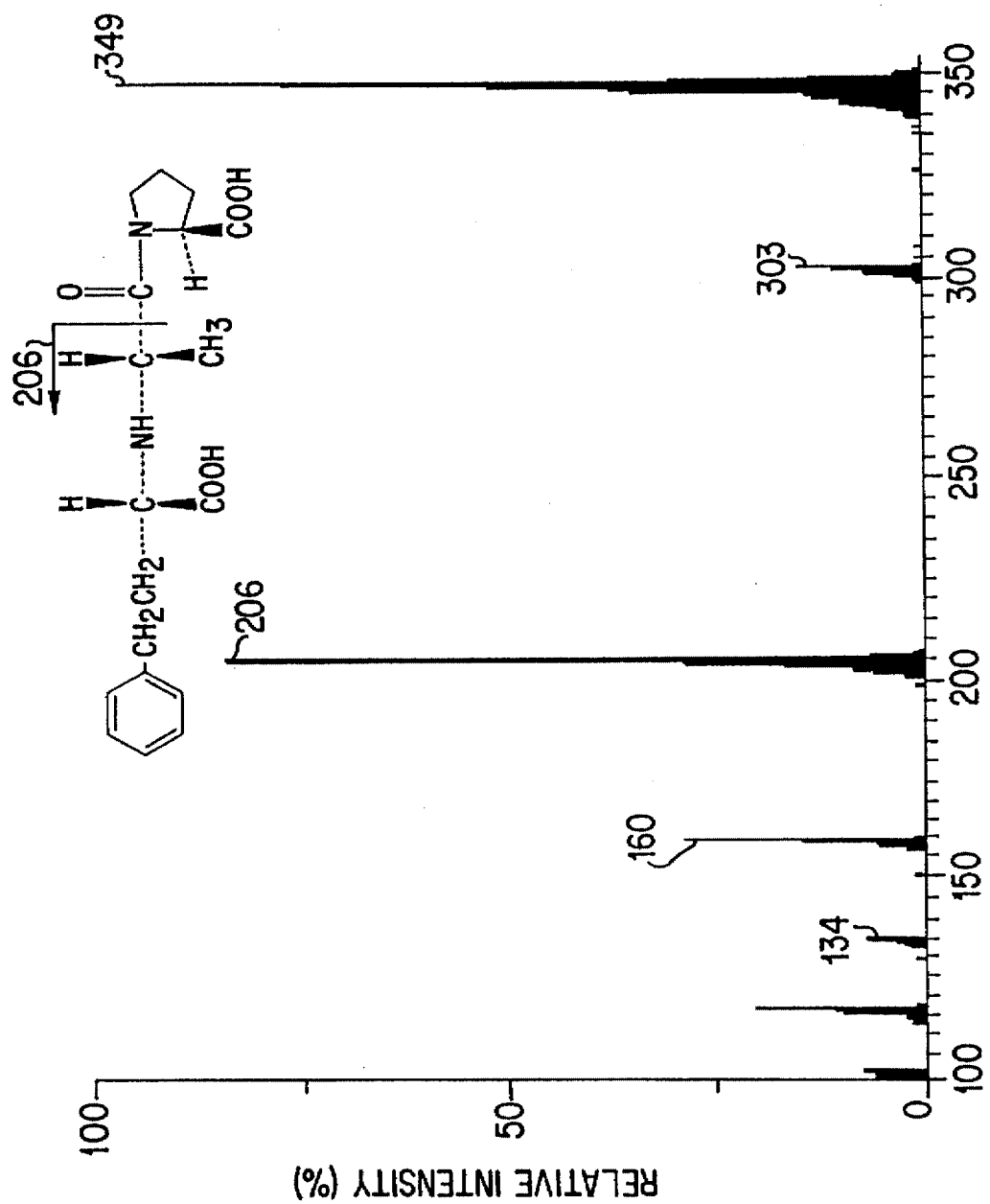
FIG. 2. LC/MS/MS product ion spectra of the two peaks labelled in the TIC profile.
Figure 2B:
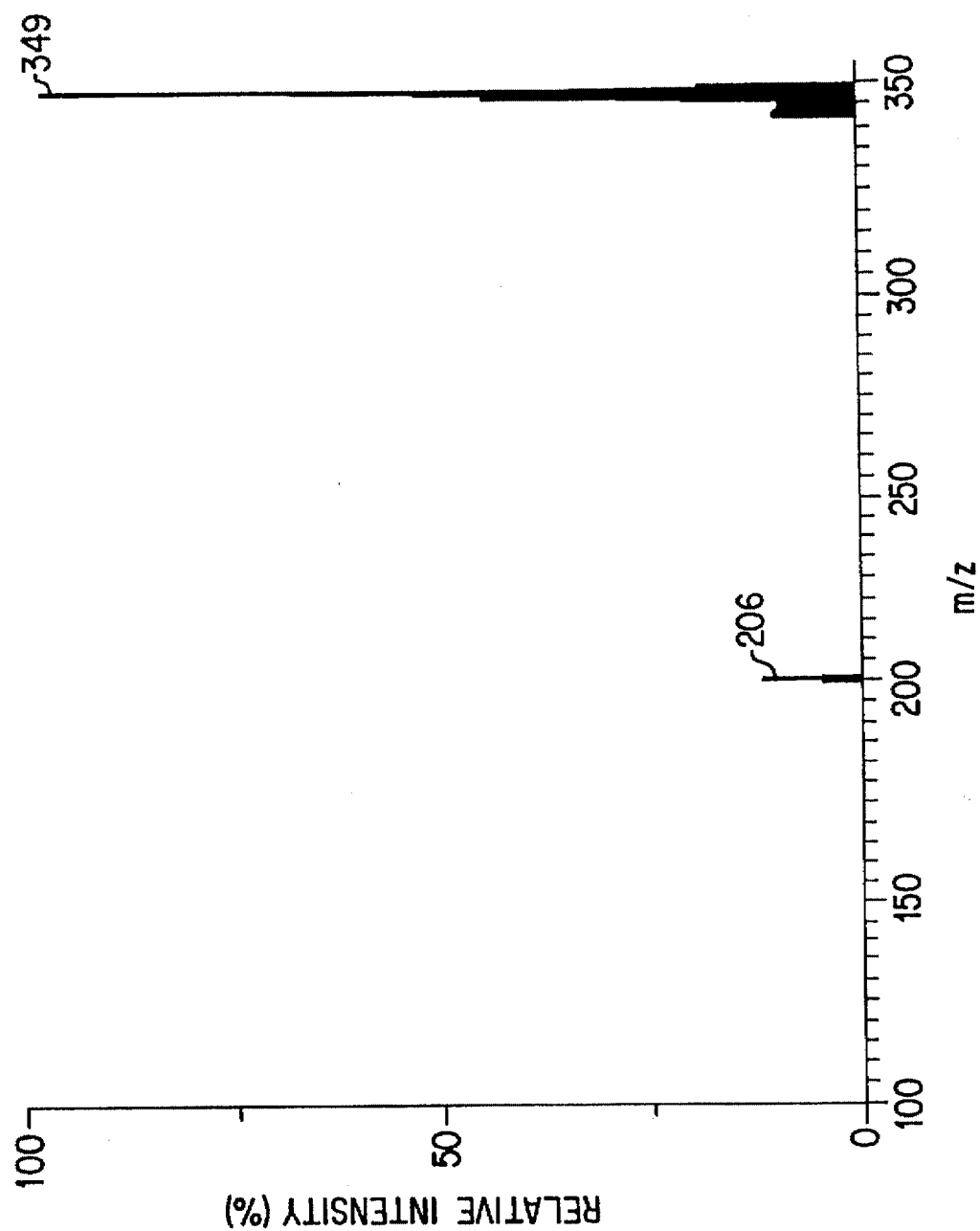

The total ion current (TIC) profile for the product ion LC/MS/MS analysis (parent at m/z 349) of the enalapril-diltiazem tablets stressed at 60° C. for four weeks is shown in FIG. 1. This profile shows that there are two peaks in this sample with a parent ion at m/z 349, the mass of the enalaprilat positive ion. Peak 1 was assigned to the enalaprilat-SSS isomer. Peak 2, a much less intense peak, was assigned to an enalaprilat isomer. The product ion spectra of these two peaks are shown in FIG. 2. The characteristic fragment ion occurring at m/z 206 was observed for both peaks 1 and 2, thereby confirming that peak 2 was due to an enalaprilat isomer. The LC/MS and LC/MS/MS results, however, did not show which isomer was formed since the molecular mass was the same for both isomers and the fragmentation of the enalaprilat isomers would also be expected to be similar.

Step D: Synthesis and Characterization of the SRS Enalaprilat Isomer

Since enalaprilat itself is SSS and the RSS isomer has been excluded from the HPLC study as discussed above, the possible assignment of the extra species to enalaprilat isomer was SRS and SSR. The SRS isomer was assigned to the extra species for the following argument. It was assumed that the SRS isomer was isomerized from enalaprilat-SSS by base catalysis in tablets. A base can abstract a proton from one of the three chiral centers of enalaprilat-SSS to form the corresponding planar carbanions. When these carbanions are protonated again, they can go back to the original isomer (enalaprilat-SSS) or change the configuration at the chiral centers. The relative formation rates of the isomers depend on the relative acidity of the three chiral centers. An examination of the relative acidity of the chiral centers indicates that the most acidic center is at the carbon 2 of enalaprilat. The protons at carbons 1 and 3 are less acidic because they are next to an acid-weakening group, a carboxyl group, while the proton at carbon 2 is the most acidic since it is adjacent to two acid-strengthening groups and a neutral methene group. ['Diketopiperazine Formation, Hydrolysis and Epimerization of the New Dipeptide Angiotensin-Converting Enzyme Inhibitor RS-10085' Gu,L., et al. Pharmaceutical Research, 1987, 4(5), 392.] Therefore, the SRS isomer is the most likely isomer to be formed.

To demonstrate that the SRS isomer can be formed through isomerization of enalaprilat-SSS by base, an enalaprilat-SSS standard was reacted with a strong base— t-butyl lithium at low temperature in tetrahydrofuran for 30 min. A reaction product was formed which had the same retention times as that of the extra species under the two sets of HPLC conditions used [35:65 and 20:80 ratios of $CH_3CN:0.001M\ KH_2PO_4$]. Accordingly, the reaction product was hypothesized to correspond to an enalaprilat isomer, most likely, the SRS-enalaprilat isomer.

Figure 3:
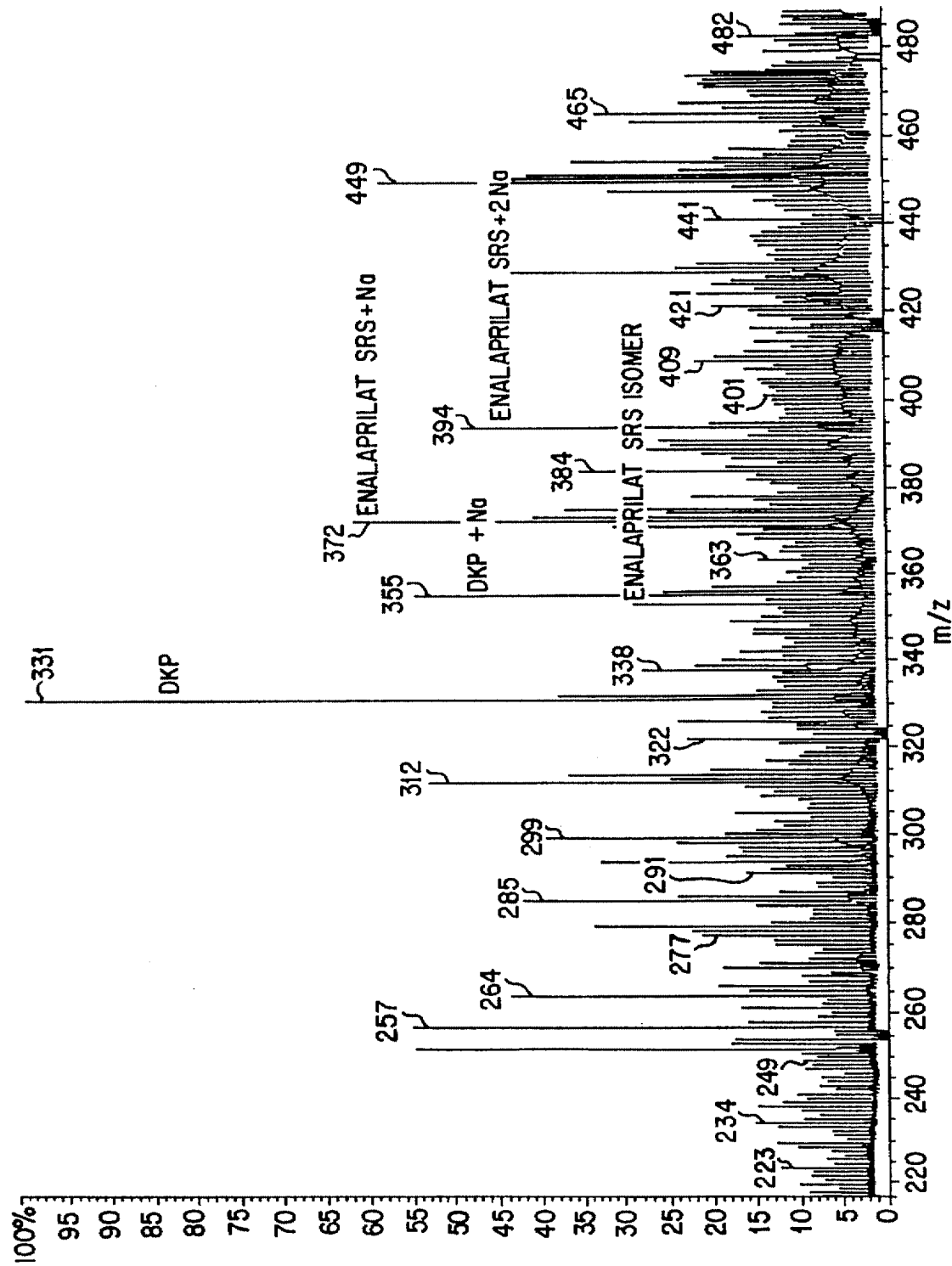
FIG. 3. FAB Mass Spectrum of SRS-enalaprilat isomer.
Figure 4:
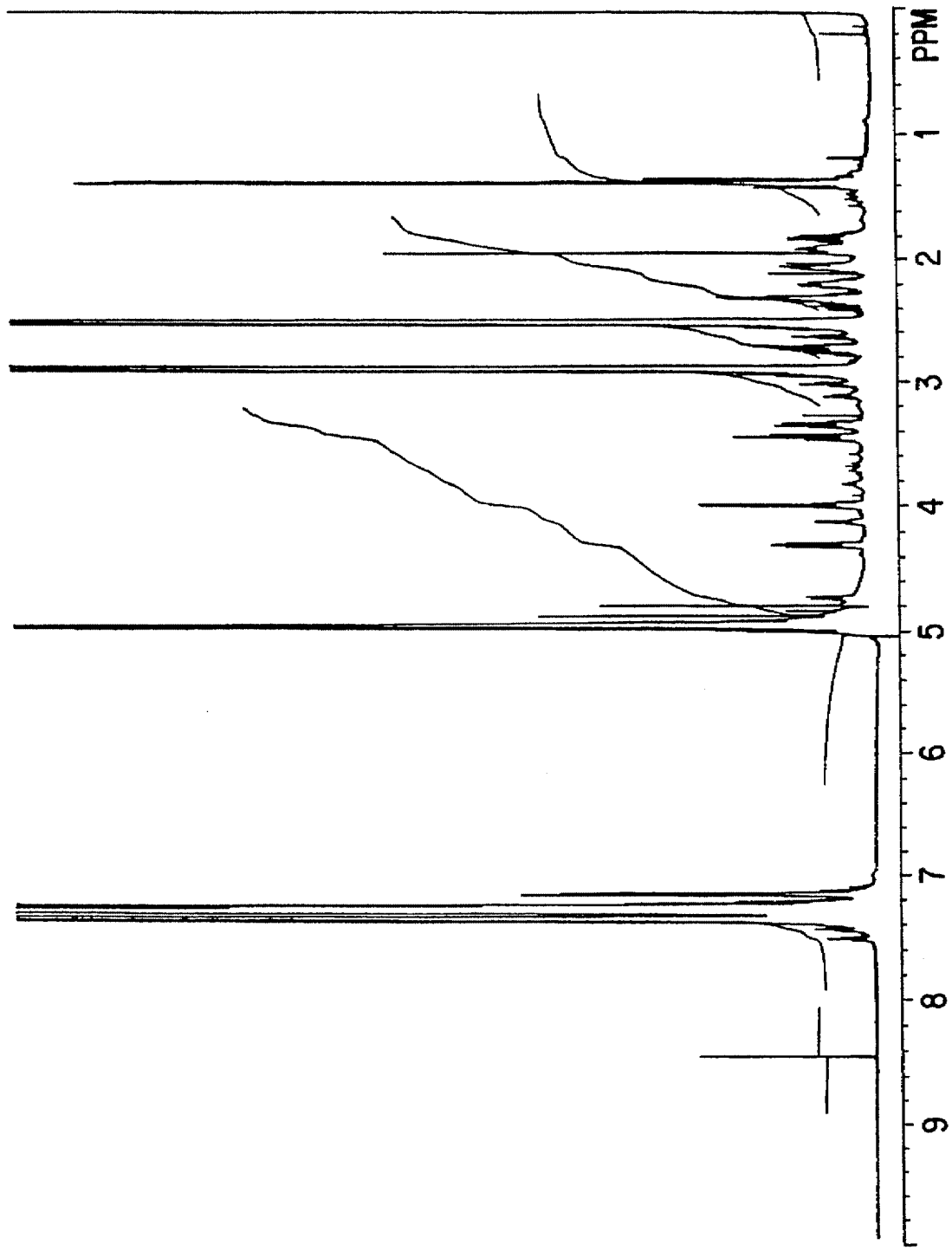
FIG. 4. $^1$H NMR Spectrum of SRS-enalaprilat isomer with tetramethylsilane.

The SRS-enalaprilat was then synthesized by (1) condensation of D—Ala—L—Pro or Ala—Pro dipeptide with ethyl 2-oxo-4-phenylbutyrate; (2) reduction of the imine bond with sodium cyanoborohydride; and (3) hydrolysis with base. ['Reductive Amination of Ethyl 2-Oxo-4-phenylbutanoate with L-Alanyl-Lproline, Synthesis of Enalappril Maleate' Wyvratt, M. J., et al. J. Org. Chem. 1984, 49, 2816-19.] The SRS enalaprilat was isolated and purified by preparative HPLC. The structural assignment of the SRS isomer was made on the basis of the mass spectrum and NMR. The FAB mass spectrum of the SRS isomer shown in FIG. 3 in the presence of potassium phosphate buffer (pH 2) (used in purification) clearly shows the protonated ions of (the SRS enalaprilat+potassium) (387), (the SRS enalaprilat+two sodium) (392.9), (the SRS enalaprilat+two potassium) (424.9), and enalaprilat-DKP degradate (331). Enalapfil-DKP was a side product of the synthesis since enalaprilat can rapidly form its DKP under acidic conditions. Also, the mass spectrum of enalaprilat-SRS using electrospray technique was taken, which clearly showed the SRS isomer, the sodium analogs of SRS, and enalaprilat-DKP. The NMR analysis of all the SRS samples showed a mixture of two components: the enalaprilat-SRS (major component) and the enalaprilat-DKP (minor component). The presence of enalaprilat-DKP did not interfere with the enalaprilat-SRS assignment. The NMR spectrum of SRS-enalaprilat is shown in FIG. 4.

Figure 5A:
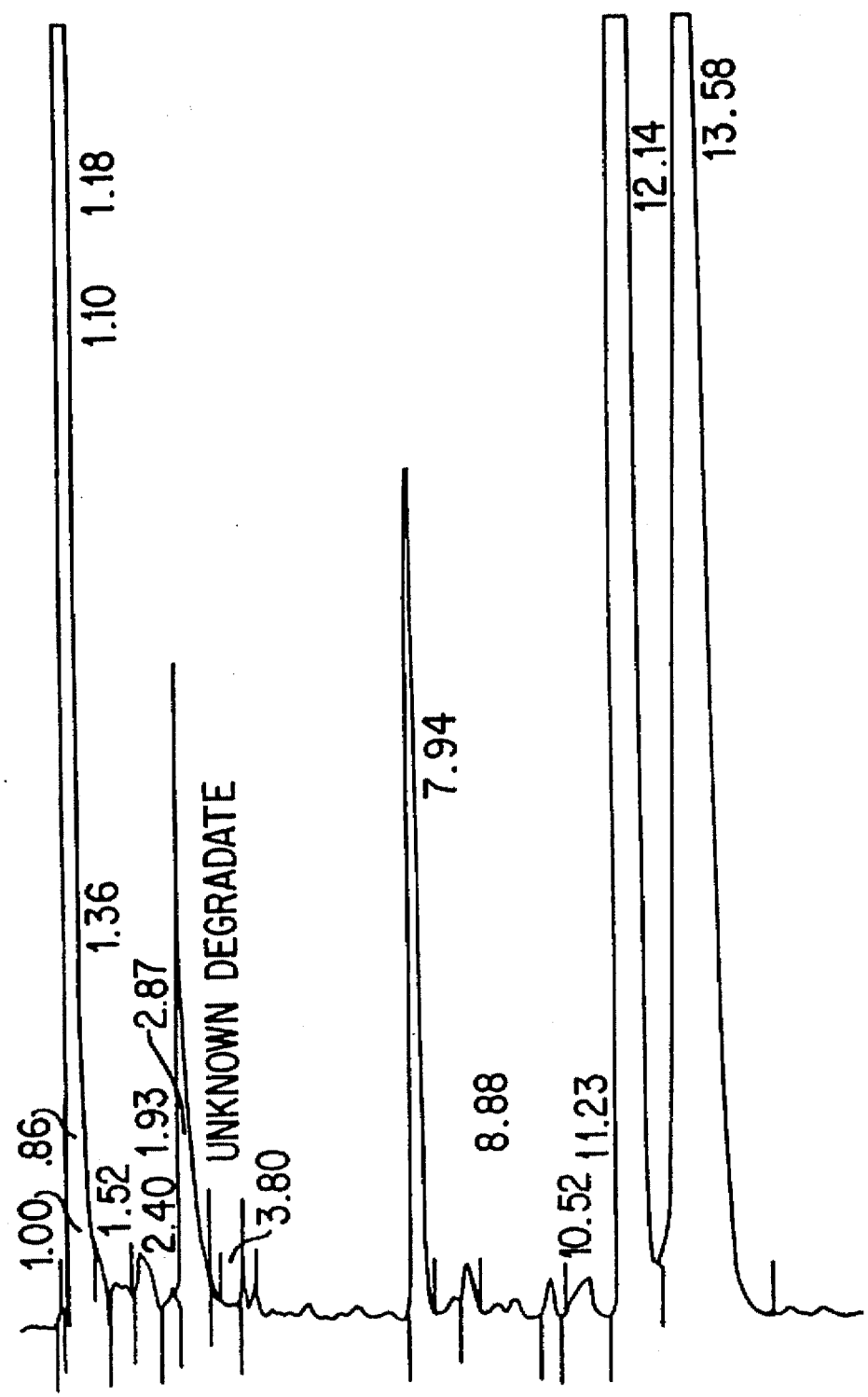
FIG. 5. HPLC Chromatograms of (a) stressed (60° C. for 4 weeks) 5/180 enalapril/diltiazem tablets and (b) SRS-enalaprilat isomer using Spherisorb C8 (5µ) 250×4.6 mm i.d. at 40° C. eluting with 35:65 CH$_3$CN to 0.001M KH$_2$PO$_4$ (at pH2) at a flow rate of 2.0 ml/min. detecting UV at 215 nm.
Figure 5B:
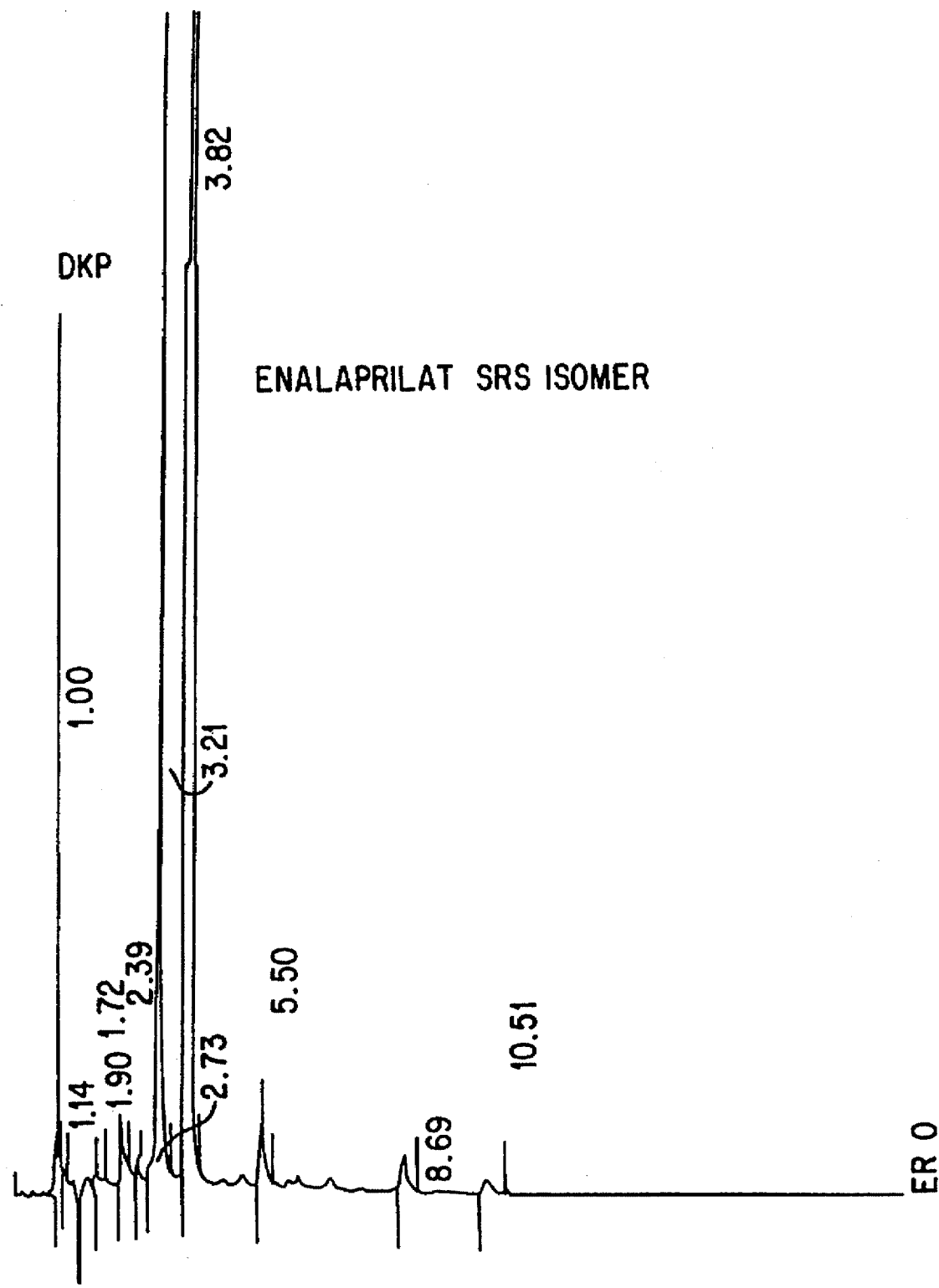
Figure 6A:
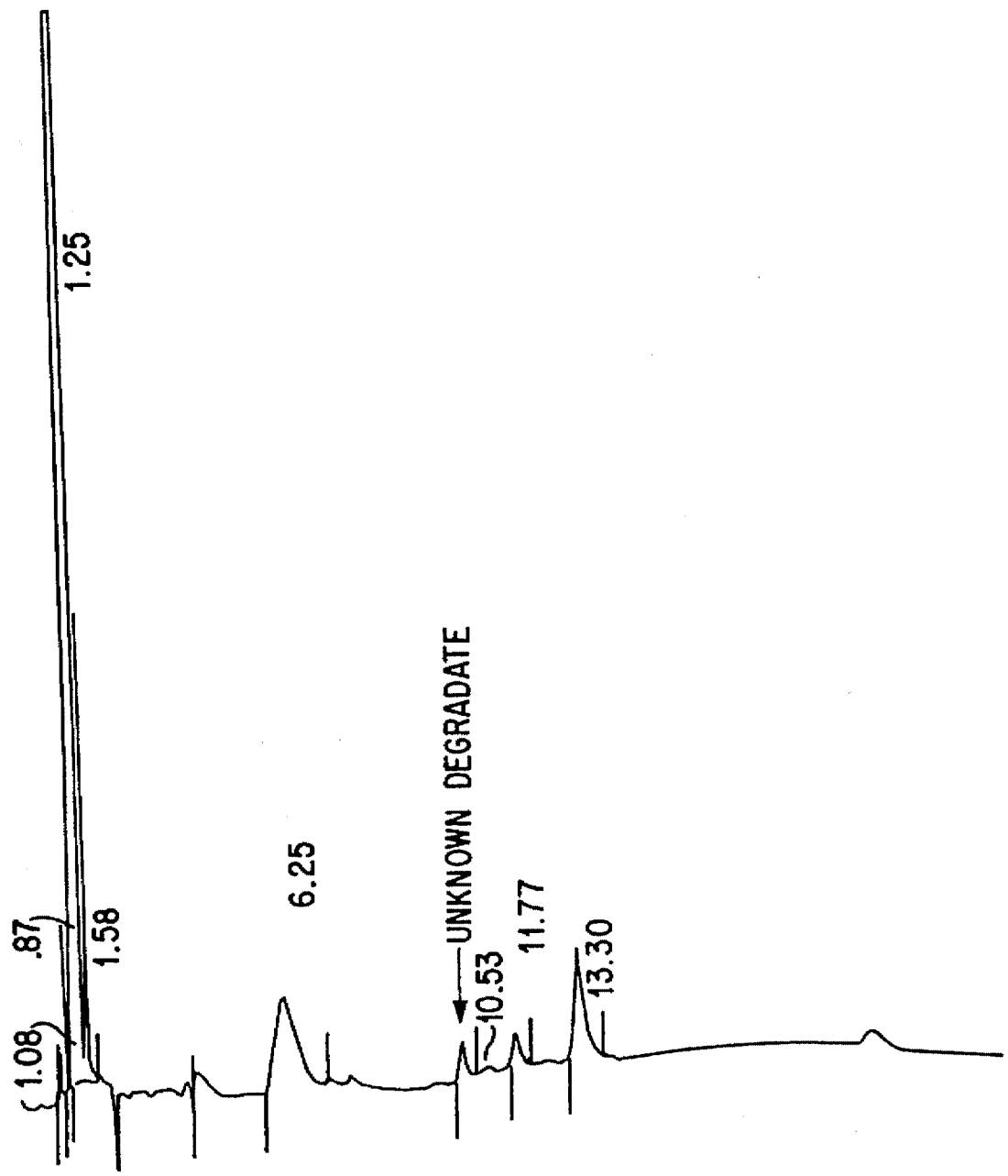
FIG. 6. HPLC Chromatograms of (a) stressed (60° C. for 4 weeks) 5/180 enalapfil/diltiazem tablets and (b) SRS-enalaprilat isomer using Spherisorb C8 (5µ) 250×4.6 mm i.d. at 40° C. eluting with 20:80 CH$_3$CN to 0.001M KH$_2$PO$_4$ (at pH2) at a flow rate of 2.0 ml/min. detecting UV at 215 nm.
Figure 6B:
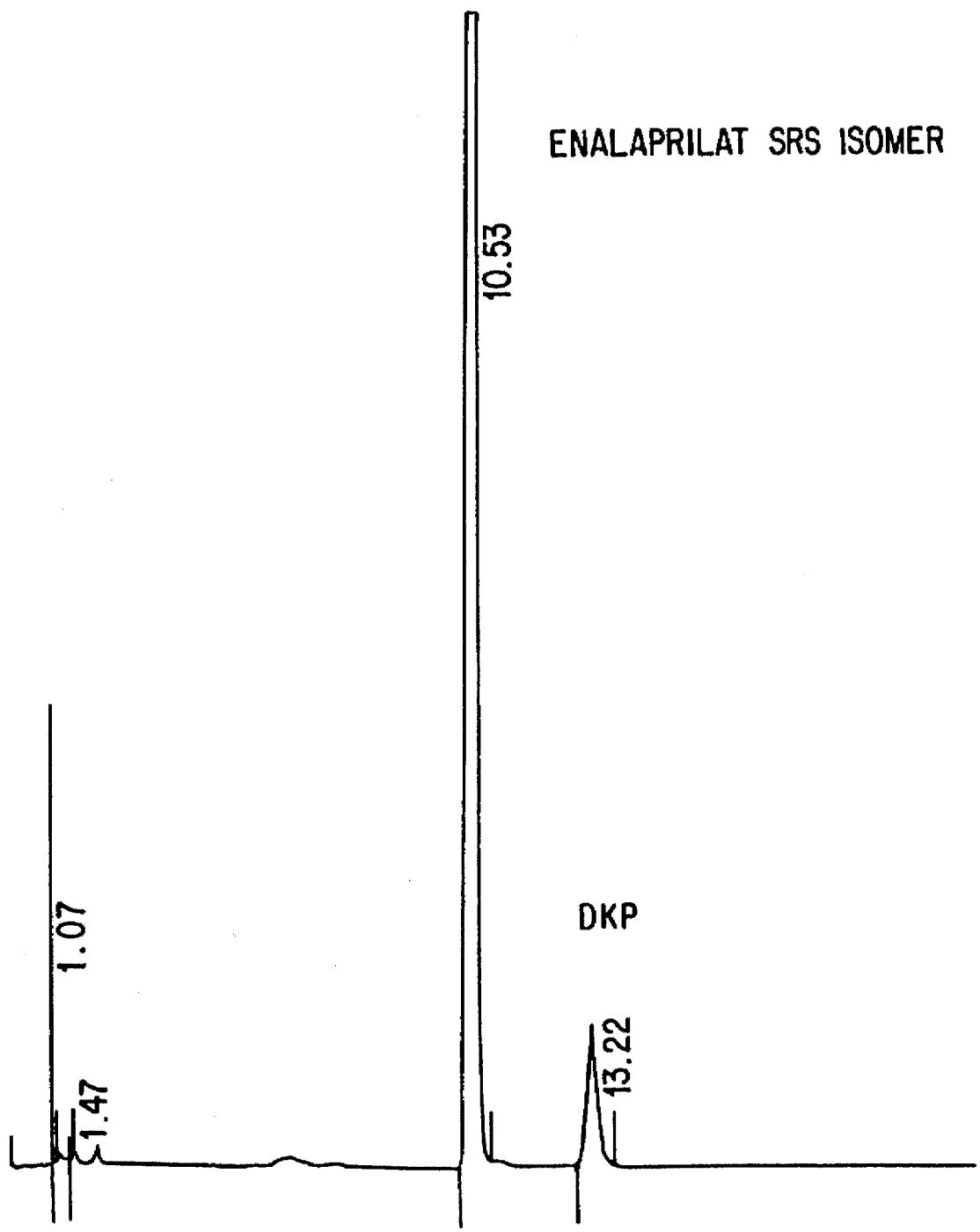

The synthesized enalaprilat-SRS matched exactly the retention times of the extra species detected in some stressed enalapril/diltiazem tablets as demonstrated in FIGS. 5 and 6.

EXAMPLE 2

Enalapril SSR

In a 50 ml round bottom flask, ethyl-2-oxo-4-phenylbutyrate (0.28 g) and L-alanyl-D-proline TFA salt (6.3 mg) were dissolved in 20 ml ethanol/water (1:1). With constant stirring and nitrogen protection, triethylamine (0.037 ml) was added to the solution and immediately after, a solution of sodium cyanoborohydride (26 mg) in 3 ml ethanol/water (1:1) was added dropwise through a syringe. The resulting mixture was stirred at room temperature for overnight, and absorbed on Dowex 2×50 W strong acid ion exchange resin. The resin was then washed with water followed by 100 ml 2% aqueous pyridine. First fraction was discarded and the rest were combined Finally, lyophilization of the combined fractions afforded enalapril SSR as a white powder. Mass spectrum: 377 (M+H), 234 (fragmentation ion).

EXAMPLE 3

Enalaprilat SSR

Enalapril SSR (Example 2) was dissolved in 20 mL 1M sodium hydroxide. The mixture was stirred overnight. The SSR diacid was isolated by preparative HPLC.

EXAMPLE 4

Enalapril SRS

In a 125 ml round bottom flask, ethyl-2-oxo-4-phenylbutyrate (0.70 ml), D-alanyl-L-proline (133.38 mg), and dry molecular sieves (5 Å, 124.92 mg) was dissolved in 50 ml absolute ethanol (a suspension was formed due to the insolubility of molecular sieves). With constant stirring and nitrogen protection, a solution of 60.10 mg sodium cyanoborohydride in 5 ml absolute ethanol was added dropwise with a syringe for one hour. The reaction mixture was then stirred at room temperature for 16 hours. The molecular sieves were removed by filtration and the filtrate was concentrated under vacuum to afford an oil which was then dispersed in 50 ml water. The pH of the solution was adjusted to 8.5 with solid dipotassium hydrogen phosphate ($K_2HPO_4$), and then extracted with ethyl acetate (3×100 ml) to remove untreated α-keto ester and α-hydroxy ester. The pH of the solution was then adjusted to 1.9 with 1M phosphoric acid (caution: this must be done in the hood !!!) and pH was maintained for 30 mins. Finally the pH of the solution was adjusted to 4.0 with dipotassium hydrogen phosphate. After saturation with sodium chloride (~13 g), the solution was extracted with ethyl acetate (2×100 ml). The combined organic layers were dried over anhydrous sodium sulfate, and concentrated under vacuum (temperature was kept at ~35° C.) to afford SRS enalapril as a foam. Mass spectrum: 377 (M+H), 234 (fragmentation ion).

EXAMPLE 5

Enalaprilat SRS

Enalapril SRS (Example 3) was dissolved in 20 mL 1M sodium hydroxide. The mixture was stirred overnight. The SRS diacid was isolated by preparative HPLC.

What is claimed is:

1. A method for analyzing the degradates of enalapril comprising:

(a) stressing a composition containing enalapfil;

(b) chromatographing the stressed composition of enalapril;

(c) comparing the chromatogram of stressed enalapril with all known enalapril degradates;

(d) analyzing the stressed composition by liquid chromatography-mass spectrometry to detect a molecular ion and fragmentation pattern for the unknown degradates;

(e) reacting a sample of enalaprilat with t-butyl lithium to form a mixture of diastereomers of enalaprilat;

(f) chromatographing the diastereomers of enalaprilat;

(g) comparing the chromatogram of stressed enalapril with the chromatogram for the mixture of diastereomers of enalaprilat;

(h) identifying the unknown enalapril degradate as a diastereomer of enalapril;

(i) synthesizing standards of enalaprilat SRS and SSR diastereomers;

(j) chromatographing the SRS and SSR diastereomers of enalapril; and (k) comparing the chromatograms of the SRS and SSR diastereomers with the chromatogram of the stressed enalapril to identify which diastereomer of enalaprilat corresponds with the unknown degradate.

2. The method for analyzing the degradates of enalapril as recited in claim 1, wherein the composition containing enalapril is stressed by exposing the composition to a temperature range of about 40° C. to about 80° C. and relative humidity of about 0 to 75% for a period of about 2.5 weeks to about 6 months.

3. The method for analyzing the degradates of enalapril as recited in claim 2, wherein the liquid chromatography is carried out using a C-8, 5µ 250×4.6 mm i.d. column using a gradient of acetonitrile and phosphate buffer.

4. The method for analyzing the degradates of enalapril as recited in claim 3, wherein the sample of enalaprilat is treated with t-butyl lithium in tetrahydrofuran for a period of about 30 minutes, followed by hydrolysis to form a mixture of diastereomers of enalaprilat.

* * * * *